(12) United States Patent
Dussich, Jr. et al.

(10) Patent No.: US 8,734,819 B2
(45) Date of Patent: May 27, 2014

(54) ANIMAL-REPELLING SYNTHETIC RESIN COMPOSITION

(76) Inventors: Joseph A. Dussich, Jr., New York, NY (US); Jeffrey A. Dussich, New York, NY (US); James A. Dussich, New York, NY (US); Joseph A. Dussich, III, New York, NY (US)

(*) Notice: Subject to any disclaimer, the term of this patent is extended or adjusted under 35 U.S.C. 154(b) by 12 days.

(21) Appl. No.: 12/822,336

(22) Filed: Jun. 24, 2010

(65) Prior Publication Data

US 2010/0260872 A1 Oct. 14, 2010

Related U.S. Application Data

(63) Continuation-in-part of application No. 11/234,082, filed on Sep. 26, 2005, now Pat. No. 7,811,597.

(60) Provisional application No. 60/612,629, filed on Sep. 24, 2004.

(51) Int. Cl.
*A01N 25/34* (2006.01)
*A01N 25/00* (2006.01)
*A01N 25/26* (2006.01)
*A61K 9/14* (2006.01)
*A01N 35/00* (2006.01)
*A61K 31/12* (2006.01)
*A01N 35/04* (2006.01)
*A61K 31/125* (2006.01)

(52) U.S. Cl.
USPC ........... 424/403; 424/405; 424/412; 424/419; 424/486

(58) Field of Classification Search
USPC .................. 424/403, 405, 412, 419, 486
See application file for complete search history.

(56) References Cited

U.S. PATENT DOCUMENTS

| | | | |
|---|---|---|---|
| 3,553,296 A * | 1/1971 | Gaeckel | 523/102 |
| 4,555,015 A | 11/1985 | Haase | |
| 4,961,929 A | 10/1990 | Gurvich et al. | |
| 5,013,551 A | 5/1991 | Atkinson | |
| 5,571,582 A | 11/1996 | Katoh | |
| 6,231,937 B1 | 5/2001 | Rader et al. | |
| 6,337,081 B1 | 1/2002 | Warberg | |
| 6,395,290 B2 | 5/2002 | Brown | |
| 2002/0094444 A1 * | 7/2002 | Nakata et al. | 428/480 |
| 2003/0055179 A1 * | 3/2003 | Ota et al. | 525/242 |
| 2006/0110421 A1 | 5/2006 | Katoh et al. | |
| 2007/0065053 A1 | 3/2007 | Feinberg | |
| 2007/0248688 A1 * | 10/2007 | La Torre | 424/581 |

FOREIGN PATENT DOCUMENTS

JP 403031203 A * 12/1991 ............. A01N 27/00

* cited by examiner

*Primary Examiner* — Mina Haghighatian
*Assistant Examiner* — Helen Chui
(74) *Attorney, Agent, or Firm* — Todd S. Sharinn; Gilbride, Tusa, Last & Spellane LLC

(57) ABSTRACT

An article, such as a container or bag for garbage, or electrical wiring insulation, which repels animals such as cats, dogs, rodents, and crows. The article is made from a synthetic resin composition including a thermoplastic polymer, and from 10 to 15,000 ppm by weight of an odorant compound such as a salicylic acid ester, menthol, corn mint oil, eucalyptus oil, and camphor, and combinations thereof. The resin composition may comprise more than one thermoplastic polymer, polyethylene and ethylene/vinyl acetate copolymer being preferred first and second thermoplastic polymers, respectively. In a method for forming the synthetic resin composition, the compound is added to the second polymer in a ratio of about 1:2 parts by weight to form a master blend that then is added to an amount of the first polymer at a master blend percentage of about 1.5%.

25 Claims, No Drawings

ANIMAL-REPELLING SYNTHETIC RESIN COMPOSITION

The present application is a Continuation-In-Part of a U.S. patent application Ser. No. 11/234,082, filed Monday, Sep. 26, 2005, now U.S. Pat. No. 7,811,597 which draws priority from a U.S. Provisional Patent Application Ser. No. 60/612,629, filed Friday, Sep. 24, 2004.

FIELD OF THE INVENTION

The present invention relates to animal-repelling materials; more particularly to articles formed of animal-repelling material; and most particularly to an improved animal-repelling article such as a garbage bag or wiring insulation and to an improved method for forming an animal-repelling synthetic resin composition at reduced cost.

BACKGROUND OF THE INVENTION

In many cities, the disposal of residential garbage is carried out as follows. Each household puts its garbage into a polyethylene garbage bag designated by the city and places the filled bag in a designated spot outside the house on an appointed day for collection. The garbage bags are then collected by city garbage trucks.

A problem associated with this conventional disposal method is that garbage bags left outside are often ripped open by foraging animals like cats, dogs, rats, squirrels, and raccoons before garbage trucks can collect them, thereby scattering the garbage.

There are similar known problems with wiring insulation. For example, in building construction, cable such as electrical cable comprising an insulator sheath made from synthetic resin typically is laid in ceilings or under floors where it is susceptible to being bitten by rats and squirrels infesting the building. As a result of the insulation being stripped off the wiring, electricity leakage, short-circuits, and fires may take place. For another example, backpackers leaving their vehicles unattended in parking lots for several days may return to find that the insulation has been chewed from the vehicle wiring harness by wild rodents.

A number of animal repellents are known, but none of them is satisfactory both in terms of effect and cost. In the prior art, repellents typically are impregnated into a powdery support, spread or sprayed directly on an article, or manufactured as a component of shaped articles having a repellent effect.

U.S. Pat. No. 5,571,582, the relevant disclosure of which is incorporated herein by reference, discloses a garbage bag or container formed of a synthetic resin composition containing 10 to 7000 ppm by weight of at least one compound selected from a group consisting of ester of salicylic acid such as methyl salicylate, ethyl salicylate, propyl salicylate, n-butyl salicylate, iso-butyl salicylate and iso-amyl salicylate, menthol and camphor. Polyolefins such as polyethylene, polypropylene, ethylene/vinyl acetate copolymer, ethylene/acrylic acid ester copolymer, and poly(1-butene) are preferable. The synthetic resin composition can be shaped into various shaped articles such as bags, bottles etc. by various methods for example extrusion, injection and blow molding. Animals such as cats, dogs, rats, and crows dislike the particular odors of ester of salicylic acid, menthol, and camphor. A repellent effect is given to shaped articles by incorporating these odorants into the synthetic resin before shaping. It was found that the repellent effect was observed if shaped articles contained more than 1 ppm by weight of these odorants, but it may be necessary that more than 10 ppm by weight of these odorants be contained in the composition for shaping in consideration of the loss during shaping. The disclosure teaches that the concentration of these odorants should be high, but if the concentration is higher than 7000 ppm bleeding may occur, so to obtain the best result, the concentration is preferably 10 to 5000 ppm by weight in the composition. If an elastomer is added to the synthetic resin composition, slow and prolonged shedding of the odorants is expected, meaning that the shaped articles comprising the composition can repel animals for a longer time.

In forming a synthetic resin composition using the odorant methyl salicylate, 20 parts by weight of methyl salicylate was added dropwise to 80 parts by weight of pellets of ethylene/vinyl acetate copolymer (EVA) ("Mitsubishi Polyethyl EVA V601S", trade name, sold by Dia Polymer Co., Ltd.) and left for 24 hours at room temperature so that methyl salicylate was impregnated into the EVA pellets. This type of blend is referred to herein as a "master blend". In the same manner, three samples of EVA pellets containing 20% by weight of ethyl salicylate, iso-butyl salicylate, and liquid menthol, respectively, were prepared. Then 2.5 parts by weight of these master blends were mixed respectively with 97.5 parts by weight of polypropylene pellets (PP) ("Mitsubishi Polypro", trade name, sold by Dia Polymer Co., Ltd.). The resulting mixed pellets were extruded and pelletized in readiness for forming into sheet form for manufacturing a garbage bag or container.

The ratio of EVA to odorant in a master blend as taught in the prior art is thus 4:1, and the odorant is impregnated into the EVA by the method of allowing the two components to stand in contact together for 24 hours.

A shortcoming of this method is that the odorant does not become well distributed through the EVA, and a relatively large percentage of EVA (which is a relatively expensive polymer), i.e., 2.5% master blend, is required to achieve the desired odorant concentration in the garbage bag or container.

Another shortcoming of this method is that the created master blend does not produce uniform absorption of odorant into the EVA, resulting in inconsistent scent strength throughout the finished product.

US Patent Application Publication US 2006/0110421, the relevant disclosure of which is incorporated herein by reference, discloses a similar composition and process for forming an article or container but extends the range of odorant composition to 10-15,000 ppm before bleeding occurs.

This reference discloses that the odorant may be incorporated into the synthetic resin composition by dropwise addition of a predetermined amount of the odorant onto pellets of the synthetic resin to be used. Thereafter, the pellets may be left alone without mixing for a predetermined amount of time at a predetermined temperature such that the odorant is impregnated into the pellets. The thus treated pellets (a master blend) may be mixed with untreated pellets to adjust the concentration of the odorant to the desired level. Preferably, the pellets treated with the odorant are left alone without mixing for a period of time ranging from several hours to 24 hours in order to have the odorant impregnated therein. Preferably, the pellets treated with the odorant are left alone at room temperature. The shortcomings of this method are noted above with respect to U.S. Pat. No. 5,571,582.

As an alternative to the dropwise addition of a predetermined amount of the odorant onto pellets of the synthetic resin, pellets of the synthetic resin may be soaked in the liquid form of the odorant. This method is wasteful because it leaves an excess of liquid odorant on the pellets that does not enhance the final activity of the synthetic resin composition in the article.

As an alternative to both dropwise addition and soaking in liquid odorant, a predetermined amount of odorant may be dissolved in a solvent, such as diethyl ether, and sprayed onto pellets of the thermoplastic polymer. The solvent may be thereafter eliminated by, e.g., air-drying at room temperature. This method is inferior because an additional compound, the solvent, is required and must be accommodated as a waste product of the process, thus increasing the manufacturing cost.

What is needed in the art is a synthetic resin composition having improved penetration of odorant into the resin that therefore can be manufactured with an overall lower level of odorant and impregnated resin, at lower cost.

What is further needed in the art is an improved method for impregnating odorant into a resin that requires less odorant, leads to more uniform distribution of odorant in the resin, and requires a lower level of master blend in the final synthetic resin composition to achieve the same or better final activity of the odorant in the article.

It is a principal object of the invention to reduce the cost of manufacture of a synthetic resin composition.

It is a further object of the invention to improve and simplify the manufacturing process for a synthetic resin composition including an animal-repelling odorant.

BRIEF DESCRIPTION OF THE INVENTION

Briefly described, the invention is directed to an article, such as a container or bag for garbage, or wiring insulation, which repels attack by animals such as cats, dogs, rats, squirrels, and raccoons. The article is made from a synthetic resin composition including a thermoplastic polymer, and from 10 to 15,000 ppm by weight of a compound such as a salicylic acid ester, menthol, corn mint oil, eucalyptus oil, and camphor, and combinations thereof. The resin composition may comprise more than one thermoplastic polymer, wherein polyethylene and ethylene vinyl acetate are the preferred first and second thermoplastic polymers.

As used herein, the terms "polymer" and "resin" may be used interchangeably.

Preferably, an article that repels animals comprises a synthetic resin composition that includes a first thermoplastic polymer and a master blend including a second thermoplastic polymer and at least one compound selected from the group consisting of a salicylic acid ester, menthol, corn mint oil, eucalyptus oil, camphor oil, and combinations thereof, wherein the ratio by weight of the second thermoplastic polymer to the compound in the master blend is between about 1.5:1 and about 3.5:1, and wherein after forming the article the compound is substantially uniformly distributed in the synthetic resin composition at between about 10 parts per million and about 15,000 parts per million by weight based on the total weight of the synthetic resin composition.

In a general method for forming the synthetic resin composition, the compound is added to the second polymer in a ratio of about 1:2 parts by weight to form a master blend. The master blend then is added to the first polymer at a master blend percentage of about 1.5%.

A currently preferred method for forming the synthetic resin composition comprises the steps of selecting first and second thermoplastic polymers; forming a master blend including the second thermoplastic polymer and a plurality of compounds selected from the group consisting of a salicylic acid ester, menthol, corn mint oil, eucalyptus oil, and camphor oil; mixing the master blend for about 48 hours in a ribbon mixer; and mixing an amount of the master blend with the amount of the first thermoplastic polymer to form the synthetic resin composition.

DETAILED DESCRIPTION OF THE INVENTION

The present invention is directed to an improved process for manufacturing an article formed from an animal-repelling synthetic resin composition, which composition is formed by combining a mixture of a first thermoplastic polymer or polymer mixture and a master blend including a second thermoplastic polymer. The polymer mixture may include an elastomer such as metallocene and further may include a filler in known fashion. In a presently preferred embodiment, the master blend forms between about 1% and about 2% and preferably about 1.5%, and the first thermoplastic polymer or polymer mixture forms between about 98% and about 99% and preferably about 98.5%, of the synthetic resin composition, as opposed to 2.5% master blend and 97.5% first thermoplastic polymer as taught by the prior art.

The second thermoplastic polymer may be identical with, or may differ from, the first thermoplastic polymer. In a presently preferred embodiment, the first thermoplastic polymer is polyethylene and the second thermoplastic polymer is ethylene/vinyl acetate copolymer (EVA). Therefore, the novel ratio of the present invention is less costly to manufacture because generally the second thermoplastic polymer is considerably more expensive than the first thermoplastic polymer.

Other specific examples of a thermoplastic polymer to be used in the invention include linear low density polyethylene (LLDPE), high pressure low density polyethylene (HPLDPE), and high density polyethylene (HDPE).

Other specific examples of an elastomer to be used in the invention include ethylene/propylene rubber (EPR), very low density polyethylene (VLDPE), hydrogenated styrene/butadiene block copolymer (SEBS), polybutadiene, ethylene/ester of acrylic acid copolymer, ethylene/butene copolymer, ethylene/1-hexene copolymer, ethylene/1-octene copolymer, butadiene/styrene copolymer, isoprene/styrene copolymer, and hydrogenated isoprene/styrene copolymer.

Specific examples of a filler to be used in the invention include diatomaceous earth, silica gel, synthetic zeolite, aluminum oxide, hydrotalcite, calcium carbonate, talc, natural zeolite, wollastonite, calcium sulfate, magnesium hydroxide, aluminum hydroxide, titanium dioxide, and carbon black.

Articles such as garbage bags, containers, and cable insulation may be formed from the synthetic resin composition of the invention by any of the procedures known in the art.

The mixed pellets may be formed into blown film, as is known in the art. For example, the mixed pellets may be formed into blown film by inflation processing at 180° C. The blown film may thereafter be cut and formed into bags by bottom sealing, as is known in the art.

Alternatively, the mixed pellets may be extruded and pelletized. The thus obtained homogenized composition may be formed into strips of film by compression molding.

The concentration of the odorant in the final article may be determined by head space gas chromatography, as is known in the art.

In certain embodiments, the synthetic resin composition may include one or both of eucalyptus oil and mint oil or corn mint oil as part of the odorant composition and further may include at least a salicylic acid ester, e.g., methyl salicylate, and camphor oil. In certain preferred embodiments, the master blend may include an intermediate odorant mixture containing from about 32% to about 40% by weight of methyl salicylate, preferably about 36%; from about 32% to about 40% by weight of corn mint oil, preferably about 36%; from about 19% to about 27% by weight of camphor oil, preferably about 23%; and from about 1% to about 8% by weight of eucalyptus oil, preferably about 5%, all based on the total weight of the odorant mixture.

A currently preferred method for forming a master blend in accordance with the present invention comprises the following steps:

a) selecting an amount of a thermoplastic polymer defined hereinabove as the second thermoplastic polymer;

b) combining a plurality of compounds selected from the group consisting of a salicylic acid ester (preferably methyl salicylate), corn mint oil, eucalyptus oil, and camphor oil to form an intermediate odorant mixture; menthol may optionally be included;

c) adding an amount of intermediate odorant mixture to the thermoplastic polymer amount in a weight ratio of between about 1.5 to about 3.5 thermoplastic polymer to 1.0 odorant mixture, and preferably about 2.0 thermoplastic polymer to 1.0 odorant mixture, to form said master blend.

Preferably, at ambient temperature the methyl salicylate is added to a mixing kettle and mixed for 5 minutes; the corn mint oil is added and the combination is mixed for another 5 minutes; the camphor white oil is added and the combination is mixed for another 5 minutes; and the eucalyptus oil is added and the combination is mixed for another 5 minutes.

In a further processing step, the assembled master blend of odorant mixture and thermoplastic polymer is mixed for up to 48 hours in a high-efficiency mixer such as a ribbon blender, which is believed to ensure substantially uniform distribution of the odorant mixture throughout the thermoplastic polymer of the master blend.

It has been found that when the master blend is prepared in this fashion, the currently-preferred weight ratio of about 2 parts thermoplastic polymer to about 1 part odorant mixture, as opposed to the ratio of 4:1 taught in the prior art, provides the same or better animal-repelling effect at lower materials cost of thermoplastic polymer.

From the foregoing description, it will be apparent that there has been provided an improved animal-repelling garbage bag or other article, and an improved method for forming a synthetic resin composition usable in forming such a garbage bag or other article. Variations and modifications of the herein described product and method for forming, in accordance with the invention, will undoubtedly suggest themselves to those skilled in this art. Accordingly, the foregoing description should be taken as illustrative and not in a limiting sense.

What is claimed is:

1. An article that repels animals, comprising a synthetic resin composition including:
a) a first thermoplastic polymer; and
b) a master blend combined with said first thermoplastic polymer wherein said master blend comprises ethylene/vinyl acetate copolymer and at least one odorant compound,
wherein the ratio by weight of said ethylene/vinyl acetate copolymer to said odorant compound in said master blend is 2:1,
wherein said first thermoplastic polymer and said ethylene/vinyl acetate copolymer are both in pellet form, and
wherein said ethylene/vinyl acetate copolymer is blended with said odorant compound through a blender for a period of time to form said master blend.

2. An article in accordance with claim 1 wherein said odorant compound is selected from the group consisting of a salicylic acid ester, menthol, corn mint oil, eucalyptus oil, camphor oil, and combinations thereof.

3. An article in accordance with claim 1 wherein said odorant compound is present in said synthetic resin composition after forming said article at between about 10 parts per million and about 15,000 parts per million by weight based on the total weight of said synthetic resin composition.

4. An article in accordance with claim 2 wherein said combination thereof comprises, by weight, 32% to 40% methyl salicylate, 32% to 40% by weight of corn mint oil, 19% to 27% by weight of camphor oil, and 1% to 8% by weight of eucalyptus oil, all based on the total weight of said combination.

5. An article in accordance with claim 2 wherein said combination comprises, by weight, 36% methyl salicylate, 36% corn mint oil, 23% white camphor oil, and 5% eucalyptus oil all based on the total weight of said combinations.

6. An article in accordance with claim 1 wherein said article is selected from the group consisting of plastic wrapping, garbage bags, and electrical wiring insulation.

7. An article in accordance with claim 1 wherein said first thermoplastic polymer comprises a polyolefin.

8. An article in accordance with claim 1 wherein said first thermoplastic polymer comprises polyethylene.

9. An article in accordance with claim 1 wherein said first thermoplastic polymer comprises an elastomer.

10. An article in accordance with claim 9 wherein said elastomer is selected from the group consisting of ethylene/propylene rubber (EPR), very low density polyethylene (VLDPE), hydrogenated styrene/butadiene block copolymer (SEBS), polybutadiene, ethylene/ester of acrylic acid copolymer, ethylene/butene copolymer, ethylene/1-hexene copolymer, ethylene/1-octene copolymer, butadiene/styrene copolymer, isoprene/styrene copolymer, metallocene, hydrogenated isoprene/styrene copolymer, and combinations thereof.

11. An article in accordance with claim 1 wherein said synthetic resin composition further comprises a filler.

12. An article in accordance with claim 11 wherein said filler is selected from the group consisting of diatomaceous earth, silica gel, synthetic zeolite, aluminum oxide, hydrotalcite, calcium carbonate, talc, natural zeolite, wollastonite, calcium sulfate, magnesium hydroxide, aluminum hydroxide, titanium dioxide, carbon black, and combinations thereof.

13. A method for forming a master blend, comprising the steps of:
a) selecting an amount of pelleted ethylene/vinyl acetate copolymer; and
b) adding an amount of at least one odorant compound to said pelleted ethylene/vinyl acetate copolymer amount in a copolymer:odorant weight ratio of 2:1, and
c) blending said ethylene/vinyl acetate copolymer and said odorant together for more than one hour in a blender.

14. A method in accordance with claim 13 wherein said odorant compound is selected from the group consisting of a salicylic acid ester, menthol, corn mint oil, eucalyptus oil, camphor oil, and combinations thereof.

15. A method in accordance with claim 14 wherein said adding step comprises the following steps:
a) adding to a vessel 36% methyl salicylate as a weight percent of said amount of odorant compound, and mixing for five minutes;
b) adding to said vessel 36% corn mint oil as a weight percent of said amount of odorant compound, and mixing for an additional five minutes;

c) adding to said vessel 23% camphor oil as a weight percent of said amount of odorant compound and mixing for an additional five minutes; and d) adding to said vessel 5% eucalyptus oil as a weight percent of said amount of odorant compound, and mixing until said combination of said odorants is uniform in composition.

16. An article in accordance with claim 1 wherein said master blend is formed in accordance with the method of claim 13.

17. A method for forming a synthetic resin composition, comprising the steps of:

a) selecting a first thermoplastic polymer;

b) forming a master blend including ethylene/vinyl acetate copolymer and at least one odorant compound;

c) blending said master blend for at least one hour in a blender; and d) combining 1.5 weight percent of said master blend with 98.5 weight percent of said first thermoplastic polymer to form said synthetic resin composition.

18. A method in accordance with claim 17 wherein said odorant compound is selected from the group consisting of a salicylic acid ester, menthol, corn mint oil, eucalyptus oil, camphor oil, and combinations thereof.

19. A method in accordance with claim 17 wherein said first thermoplastic polymer comprises polyethylene.

20. A method in accordance with claim 18 wherein said combination thereof comprises 36% methyl salicylate, 36% corn mint oil, 23% white camphor oil, and 5% eucalyptus oil, all as weight percentages based on the total weight of said combinations.

21. A method in accordance with claim 17 wherein said ethylene/vinyl acetate copolymer and said at least one odorant compound are present in said master blend in a copolymer:odorant weight ratio of 2:1.

22. An article in accordance with claim 1 wherein said synthetic resin composition is formed in accordance with the method of claim 17.

23. An article that repels animals comprising a synthetic resin composition including:

a) a first thermoplastic polymer; and b) a master blend including ethylene/vinyl acetate copolymer and at least one odorant compound, wherein the percentage by weight of said master blend is between 1.0% and 2.0% and the percentage by weight of said first thermoplastic polymer is between 99.0% and 98.0% in said synthetic resin composition, and wherein said ethylene/vinyl acetate copolymer is combined with said odorant compound through a blending device before being combined with said first thermoplastic polymer.

24. An article in accordance with claim 23 wherein said odorant compound is selected from the group consisting of a salicylic acid ester, menthol, corn mint oil, eucalyptus oil, camphor oil, and combinations thereof.

25. An article in accordance with claim 23 wherein the percentage by weight of said master blend is 1.5% and the percentage by weight of said first thermoplastic polymer is 98.5% in said synthetic resin composition.

* * * * *